US012648570B2

(12) United States Patent
Kwon et al.

(10) Patent No.: US 12,648,570 B2
(45) Date of Patent: Jun. 9, 2026

(54) ***RHIZOPUS OLIGOSPORUS* STRAIN AND ANTIMICROBIAL COMPOSITION INCLUDING THE SAME**

(71) Applicant: CJ CHEILJEDANG CORPORATION, Seoul (KR)

(72) Inventors: Hyelim Kwon, Seoul (KR); Hyungseok Ryu, Seoul (KR); Hee-Su Kwon, Seoul (KR); Eun Jung Jeon, Seoul (KR); Jiyoung Oh, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 61 days.

(21) Appl. No.: 18/273,347

(22) PCT Filed: Mar. 29, 2021

(86) PCT No.: PCT/KR2021/003829
§ 371 (c)(1),
(2) Date: Jul. 20, 2023

(87) PCT Pub. No.: WO2022/158641
PCT Pub. Date: Jul. 28, 2022

(65) Prior Publication Data
US 2024/0117294 A1    Apr. 11, 2024

(30) Foreign Application Priority Data
Jan. 22, 2021    (KR) ........................ 10-2021-0009548

(51) Int. Cl.
*A01N 63/30*    (2020.01)
*A23B 2/783*    (2025.01)
*A23L 11/50*    (2021.01)
*A61K 36/06*    (2006.01)
*C12N 1/145*    (2026.01)
*C12R 1/845*    (2006.01)

(52) U.S. Cl.
CPC .............. *A01N 63/30* (2020.01); *A23B 2/783* (2025.01); *A23L 11/50* (2021.01); *A61K 36/06* (2013.01); *C12N 1/145* (2021.05); *C12R 2001/845* (2021.05)

(58) Field of Classification Search
CPC .......... C12N 1/145; C12N 1/14; A01N 63/30; A23B 2/783; A61K 36/06; A61K 8/99; C12R 2001/845; C12R 2001/645; A01P 1/00; A61P 31/00; A23K 10/18; A23L 33/135
See application file for complete search history.

(56) References Cited

FOREIGN PATENT DOCUMENTS

KR    10-2013-0061448 A    6/2013

OTHER PUBLICATIONS

Kobayasi, S et al. Purification and characterization of an antibiotic substance produced from Rhizopus oligosporus IFO 8631. Biosci. Biotech. Biochem. 1992. 56(1): 94-98. (Year: 1992).*

Yamada, O et al. Cloning and heterologous expression of the antibiotic peptide (ABP) genes from Rhizopus oligosporus NBRC 8631. Biosci. Biotechnol. Biochem. 2005. 69(3): 477-482. (Year: 2005).*

Aoki, H et al. The production of a new tempeh-like fermented soybean containing a high level of gamma-aminobutyric acid by anaerobic incubation with Rhizopus. Biosci. Biotechnol. Biochem. 2003. 67(5): 1018-1023. (Year: 2003).*

'Seq ID No. 2 Search in GenEmbl database.' GenEmbl database. OM nucleic-nucleic search. Performed on Aug. 22, 2025. (Year: 2025).*

BLAST. Alignment of AB016015 with Seq ID No. 1. [online] 2025 [retrieved on Aug. 27, 2025]. Retrieved from the Internet: <URL: https://blast.ncbi.nlm.nih.gov/Blast.cgi#> (Year: 2025).*

Yanai, K et al. Purification of two chitinases from Rhizopus oligosporus and isolation and sequencing of the encoding genes. Journal of Bacteriology. 1992. 174(22): 7398-7406. (Year: 1992).*

'Seq ID No. 3 Search in GenEmbl database.' GenEmbl database. OM nucleic-nucleic search. Performed on Aug. 22, 2025. (Year: 2025).*

Tang, J et al. Incidence and characterization of *Staphylococcus aureus* strains isolated from food markets. Ann. Microbiol. 2015. 65: 279-286. (Year: 2015).*

Wang, HL et al. Mass production of Rhizopus oligosporus spores and their application in tempeh fermentation. Journal of Food Science. 1975. 40: 168-170. (Year: 1975).*

Abdel Hameed, AA et al. Fungi and some mycotoxins producing species in the air of soybean and cotton mills: a case study. Atmospheric Pollution Research. 2012. 3: 126-131. (Year: 2012).*

Park, KM et al. Occurrence of toxigenic Bacillus cereus and Bacillus thuringiensis in doenjang, a Korean fermented soybean paste. Journal of Food Protection. 2016. 79(4): 605-612. (Year: 2016).*

Bajpai et al., "Antifungal Properties of Rhizopus oligosporus Against Apple Anthracnose Fungi," Korean Journal of Environmental Agriculture, 29(1): 86-91 (2010).

Chen et al., "Effects of Red-Bean Tempeh with Various Strains of Rhizopus on GABA Content and Cortisol Level in Zebrafish," Microorganisms, 8(1330): 1-12 (2020).

Kiers et al., "Inhibition of adhesion of enterotoxigenic *Escherichia coli* K88 by soya bean tempe," Letters in Applied Microbiology, 35: 311-315 (2002).

Roubos-Van Den Hil et al., "Soya bean tempe extracts show antibacterial activity against Bacillus cereus cells and spores," Journal of Applied Microbiology, 109: 137-145 (2010).

International Search Report issued in corresponding International Patent Application No. PCT/KR2021/003829 dated Oct. 22, 2021.

Lianxiang et al., "Fermentation Conditions and Properties of the Antibiotic Substance Produced by Rhizopus chinesis 12", Food and Fermentation Industries, vol. 24, No. 1, 1998, pp. 7-10, with an English Abstract.

(Continued)

*Primary Examiner* — David W Berke-Schlessel
*Assistant Examiner* — Susan E. Fernandez
(74) *Attorney, Agent, or Firm* — Morgan, Lewis & Bockius LLP

(57)    ABSTRACT

The present application relates to a *Rhizopus oligosporus* CJCC02-20 strain deposited with Accession No. KCCM12893P and application thereof.

14 Claims, 1 Drawing Sheet

Specification includes a Sequence Listing.

(56)          References Cited

OTHER PUBLICATIONS

Masrianti et al., "Rhizopus oligosporus Activity in Crude Extract and Powder Form to Reduce Aspergillus flavus and Aflatoxin Contamination in Corn", JITV, vol. 24, No. 4, 2019, pp. 173-181.
Fadahunsi et al., "Heat Stability and Optimization of Invitro Anti-microbial Activity of Metabolites Produced By Rhizopus Oligosporus NRRL 2710 Against Some Pathogenic Bacteria", Trakia Journal of Sciences, vol. 11, Issue 2, 2013, 1 page.

* cited by examiner

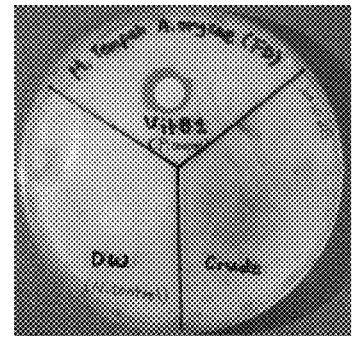
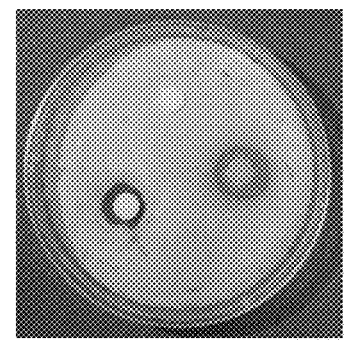
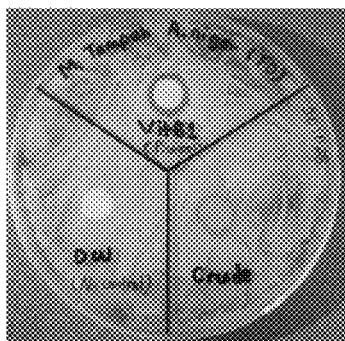
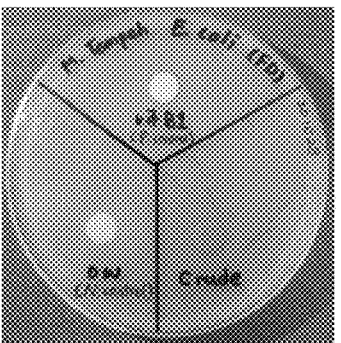

RHIZOPUS OLIGOSPORUS STRAIN AND ANTIMICROBIAL COMPOSITION INCLUDING THE SAME

A computer readable xml file, entitled "133660-04-9005-US_Sequence_Listing_ST25.TXT," created on or about Aug. 13, 2025, with a file size of 8,460 bytes contains the sequence listing for this application and is hereby incorporated by reference in its entirety.

TECHNICAL FIELD

The present application relates to a *Rhizopus oligosporus* CJCC02-20 strain deposited with Accession No. KCCM12893P; an antimicrobial composition including any one or more selected from the group consisting of the strain, a spore of the strain, a culture of the strain, a concentrate thereof, and a dried product thereof as an active ingredient; a food composition including the antimicrobial composition; a feed composition; a quasi-drug composition; a health functional food composition; or a pharmaceutical composition for preventing or treating microbial infectious diseases caused by fungi, bacteria, or a combination thereof, which includes the antimicrobial composition.

BACKGROUND ART

Fermented foods manufactured in traditional way are always vulnerable to fungi and food poisoning bacteria in the process of storing, manufacturing, and distributing raw materials. It is known that fungi and food poisoning—causing bacteria can survive even after heat treatment, causing deterioration and spoilage of food, or food poisoning.

In order to prevent deterioration and growth of food poisoning bacteria, and to maintain the quality of the food for long time, many studies have been conducted on anti-microbial substances. Among antimicrobial substances, there is an increasing need for research on natural preservatives with excellent safety and economic feasibility in particular.

As a representative natural preservative, bacteriocins refer to natural antimicrobial proteins or protein-based materials produced by microorganisms. Bacteriocins have been proved to be safe because they are proteins that can be degraded in the human body. This implies that the need for research on bacteriocins is increasing in contrast to the secondary metabolites of existing antibiotics that cause side effects in the human body. With respect to the bacteriocins, studies have thus far been conducted mainly on lactic acid bacteria-derived bacteriocins. Although the lactic acid bacteria-derived bacteriocins have been granted GRAS (generally recognized as safe) designation, they are not widely used because their antimicrobial activity range is specific to Gram-positive bacteria.

With regard to the antimicrobial properties of *Rhizopus oligosporus*, antibiotic peptides (ABP) and linoleic acid, which are antimicrobial substances produced from the culture broth of *Rhizopus oligosporus*, are known to control Gram-positive bacteria belonging to the genus of *Staphylococcus* and *Bacillus* (Roubos-van den Hil et al., 2010). However, the antimicrobial activity against specific Gram-positive microorganisms has only been reported, and no effect on various strains causing deterioration or food poisoning has been reported. Further, *Rhizopus oligosporus* is a useful bacterium in fermented foods, and thus, when the bacteriocins are applied to fermented foods, they might not exhibit a specific activity against deterioration-causing fungi and food poisoning bacteria, and therefore it is difficult to industrialize fermented foods to be manufactured and distributed.

DISCLOSURE

Technical Problem

Accordingly, the present inventors have made extensive efforts to develop a method for inhibiting various fungi and bacteria, while remaining harmless to the human body, and as a result, they have confirmed that *Rhizopus oligosporus* CJCC02-20, a novel strain isolated from tempeh, not only has an antimicrobial activity against fungi, but also shows an antimicrobial activity that specifically inhibits only major harmful microorganisms in food, such as food poisoning bacteria, thereby completing the present application.

Technical Solution

The present application relates to a *Rhizopus oligosporus* CJCC02-20 strain deposited with Accession No. KCCM12893P, an antimicrobial composition including any one or more selected from the group consisting of the strain, a spore of the strain, a culture of the strain, a concentrate thereof, and a dried product thereof as an active ingredient; a food composition including the antimicrobial composition; a feed composition; a quasi-drug composition; a health functional food composition; or a pharmaceutical composition for preventing or treating microbial infectious diseases caused by fungi, bacteria, or a combination thereof, which includes the antimicrobial composition.

It is one object of the present application to provide a *Rhizopus oligosporus* CJCC02-20 strain deposited with Accession No. KCCM12893P.

It is another object of the present application to provide an antimicrobial composition, including any one or more selected from the group consisting of the *Rhizopus oligosporus* CJCC02-20 strain, a spore of the strain, a culture of the strain, a concentrate thereof, and a dried product thereof as an active ingredient.

It is still another object of the present application to provide a food composition including the antimicrobial composition.

It is yet another object of the present application to provide a feed composition including the antimicrobial composition.

It is even another object of the present application to provide a quasi-drug composition including the antimicrobial composition.

It is further another object of the present application to provide a health functional food composition including the antimicrobial composition.

It is still further another object of the present application to provide a pharmaceutical composition for preventing or treating microbial infectious diseases caused by fungi, bacteria, or a combination thereof, which includes the antimicrobial composition.

Advantageous Effects

The antimicrobial composition including the *Rhizopus oligosporus* CJCC02-20 strain according to the present application has an antimicrobial activity against fungi and bacteria, and thus can be effectively used in food, pharmaceuticals, quasi-drugs, health functional foods, etc.

BRIEF DESCRIPTION OF DRAWING

FIG. 1 is a result of measuring the antimicrobial activity of the *Rhizopus oligosporus* CJCC02-20 strain against *Aspergillus oryzae, Aspergillus niger*, and *Escherichia coli* using a paper disk assay.

DETAILED DESCRIPTION OF EMBODIMENTS

Hereinbelow, the present application will be described in detail. Meanwhile, each of the explanations and exemplary embodiments disclosed herein can be applied to other explanations and exemplary embodiments. That is, all combinations of various factors disclosed herein belong to the scope of the present application. Furthermore, the scope of the present application should not be limited by the specific disclosure provided hereinbelow.

Additionally, those of ordinary skill in the art may be able to recognize or confirm, using only conventional experimentation, many equivalents to the particular aspects of the invention described herein. Furthermore, it is also intended that these equivalents be included in the present application.

In order to achieve the objects above, one aspect of the present application provides a *Rhizopus oligosporus* CJCC02-20 strain deposited with Accession No. KCCM12893P.

The present inventors have identified a novel strain belonging to *Rhizopus oligosporus* having an excellent antimicrobial activity against fungi that cause deterioration and contamination of fermented foods and food poisoning—causing bacteria, as follows.

Various types of *Rhizopus oligosporus* were isolated from the traditional tempeh and tested for fungi, such as mold and yeast, and food poisoning bacteria, and as a result, the *Rhizopus oligosporus* strain with excellent antimicrobial activity was selected, and the gene sequencing was carried out to identify the selected strain. The 18S rRNA nucleotide sequence of the selected strain was represented by SEQ ID NO: 1, the ABP (antibiotic peptide) gene sequence was represented by SEQ ID NO: 2, and the Chitinase (Chi2) gene sequence was represented by SEQ ID NO: 3. Based on the gene analysis, the strain was identified as a *Rhizopus oligosporus* strain, named *Rhizopus oligosporus* CJCC02-20, and deposited at the Korean Culture Center of Microorganisms (KCCM), an International Depositary Authority, under the Budapest Treaty on Dec. 9, 2020, with Accession No. KCCM12893P.

According to one embodiment of the present application, the newly isolated *Rhizopus oligosporus* CJCC02-20 has an excellent antimicrobial activity against fungi and food poisoning—causing bacteria, and thus exhibits an antimicrobial activity that can simultaneously act on various fungi and food poisoning—causing bacteria (Example 3).

The fungi and bacteria may be microorganisms belonging to the genus of *Aspergillus, Bacillus*, or *Escherichia*, but are not limited thereto.

In one embodiment of the present application, the *Rhizopus oligosporus* CJCC02-20 may have an antimicrobial activity against *Aspergillus oryzae, Aspergillus niger*, both of which are fungi, or a combination thereof, but the types of fungi are not limited thereto.

In one embodiment of the present application, the *Rhizopus oligosporus* CJCC02-20 may have an antimicrobial activity against *Bacillus cereus, Escherichia coli*, or a combination thereof, but the types of bacteria are not limited thereto.

In one embodiment of the present application, the *Rhizopus oligosporus* CJCC02-20 may have a specific antimicrobial activity against *Aspergillus oryzae, Aspergillus niger*, or *Escherichia coli*, but is not limited thereto.

The *Aspergillus oryzae* and *Aspergillus niger* are known as strains that cause degradation and contamination of fermented foods, and *Bacillus cereus* and *Escherichia coli* are known as food poisoning—causing bacteria, and thus, the *Rhizopus oligosporus* CJCC02-20, which has an excellent antimicrobial activity against those microorganisms, can be used for various purposes.

As another aspect to achieve the objects above, the present application provides a composition including any one or more selected from the group consisting of the newly isolated *Rhizopus oligosporus* CJCC02-20 strain, a spore of the strain, a culture of the strain, a concentrate thereof, an extract thereof, and a dried product thereof; and a carrier.

In particular, the carrier may be a naturally occurring carrier or one which is not naturally occurring.

In one embodiment of the present application, the dried product may be a freeze-dried product.

Additionally, the composition may further include a cryoprotectant. For example, the composition may further include at least one cryoprotectant selected from the group consisting of glycerol, trehalose, maltodextrin, skim milk powder, and starch. The cryoprotectant of the present application may be contained in an amount of 0.01% to 20% by weight and 0.01% to 10% by weight based on the total weight of the composition. Specifically, the glycerol may be contained in an amount of 5% to 20% by weight, the trehalose may be contained in an amount of 2% to 10% by weight, the maltodextrin may be contained in an amount of 2% to 10% by weight, the skim milk powder may be contained in an amount of 0.5% to 2% by weight, and the starch may be contained in an amount of 0.1% to 1% by weight in the composition.

As still another aspect to achieve the objects above, the present application provides an antimicrobial composition including any one or more selected from the group consisting of the newly isolated *Rhizopus oligosporus* CJCC02-20 strain, a spore of the strain, a culture of the strain, a concentrate thereof, an extract thereof, and a dried product thereof as an active ingredient.

In particular, the strain may be in a liquid state or a dry state, but is not limited thereto.

The antimicrobial composition may have an antimicrobial activity against fungi, bacteria, or a combination thereof, and specifically, it may have a specific antimicrobial activity against *Aspergillus oryzae, Aspergillus niger*, or *Escherichia coli*, and may have an enhanced antimicrobial activity against *Bacillus cereus*, but is not limited thereto.

As used herein, the term "spore" refers to the reproductive cells of bacteria, etc. For the purpose of the present application, the spore means the reproductive cells of the *Rhizopus oligosporus* CJCC02-20 strain.

In the present application, the spore of the *Rhizopus oligosporus* CJCC02-20 exhibits an antimicrobial activity against fungi and food poisoning bacteria, and thus can be used by being contained in foods, feeds, pharmaceuticals, quasi-drugs, and health functional foods having antimicrobial activity.

As used herein, the term "culture" refers to a product obtained after culturing the strain, and may be an undiluted culture containing cells or may be a cultured strain, or cells obtained by removing or concentrating the culture supernatant. The composition of the culture may further contain not only components necessary for conventional culturing of *Rhizopus oligosporus*, but also components that synergistically act on the growth of *Rhizopus oligosporus*, and the resulting composition may be easily selected by those of ordinary skill in the art.

As used herein, the term "concentrate" refers to that which is obtained by concentrating the culture.

As used herein, the term "extract" refers to that which is obtained by extraction from the culture or a concentrate thereof, and may include all of an extract, a dried product obtained by drying a dilution or concentrate of the extract, and an extract, or a crude product or purified product thereof, or a fraction obtained by fractionating the same, as long as it is an extract that can exhibit a specific antimicrobial effect on fungi and bacteria of the present application.

As used herein, the term "dried product" refers to that which is obtained by drying the culture, a concentrate thereof, an extract thereof, or a fraction thereof. The drying method may be air-drying, natural drying, spray-drying, and freeze-drying, but is not limited thereto.

The newly isolated *Rhizopus oligosporus* CJCC02-20 of the present application can be cultured by way of a conventional method for culturing *Rhizopus oligosporus* strains, but the method is not limited thereto. As the medium, a natural medium or a synthetic medium can be used. As the carbon source of the medium, for example, glucose, sucrose, dextrin, glycerol, starch, etc. may be used. As the nitrogen source, peptone, meat extracts, yeast extracts, dried yeast, soybean, ammonium salts, nitrate and other organic or inorganic nitrogen-containing compounds may be used, but the components are not limited thereto. As the inorganic salts included in the medium, magnesium, manganese, calcium, iron, potassium, etc. may be used, but the inorganic salts are not limited thereto. Amino acids, vitamins, nucleic acids, and related compounds may be added to the medium in addition to the carbon source, the nitrogen source, and the components of the inorganic salts.

The antimicrobial composition may include other by-products produced in the process of culturing *Rhizopus oligosporus* CJCC02-20.

As yet another aspect to achieve the objects above, the present application provides a food composition including the antimicrobial composition.

There is no particular limitation on the types of the food, and it may include all foods in the ordinary sense. Non-limiting examples of foods to which the above material can be added include fermented food including Korean paste and salted fish, meats, sausages, bread, chocolates, candies, snacks, confectionaries, pizzas, instant noodles, other noodles, gums, dairy products including ice creams, various kinds of soup, beverages, teas, drinks, alcoholic drinks, vitamin complexes, etc. When the composition is used as a food additive, the composition may be added as it is or used together with other components, and may be appropriately used according to a conventional method.

Specifically, the food composition may be a fermented food, and specifically Korean paste or salted fish, and more specifically tempeh, but is not limited thereto.

Additionally, the food composition may be a sauce including tempeh, but is not limited thereto.

The food composition may include a sitologically acceptable carrier.

The type of the carrier is not particularly limited, and any carrier commonly used in the art may be used.

In addition, the food composition may further include additional ingredients which may be conventionally used in food compositions to improve smell, taste, and sight. For example, it may include vitamins A, C, D, E, $B_1$, $B_2$, $B_6$, and $B_{12}$, niacin, biotin, folate, pantothenic acid, etc. Additionally, the food composition may further include minerals such as Zn, Fe, Ca, Cr, Mg, Mn, Cu, Cr, etc., and amino acids such as lysine, tryptophan, cysteine, valine, etc.

Further, the food composition may further include food additives such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclamate, saccharin, sodium, etc.), flavors (vanillin, lactones, etc.), swelling agents (alum, potassium D-hydrogen tartrate, etc.), fortifiers, emulsifiers, thickeners (adhesive pastes), film-forming agents, gum base agents, antifoaming agents, solvents, improvers, dispersants, etc. These food additives may be selected according to the types of food and used in an appropriate amount.

In particular, the present inventors confirmed that the newly isolated *Rhizopus oligosporus* CJCC02-20 of the present application has an effect of simultaneously inhibiting *Aspergillus oryzae*, a fermentative fungus for Korean paste, *Aspergillus niger*, a food contaminant, *Bacillus cereus*, a food poisoning bacterium, and *Escherichia coli*, which is an enteropathogenic bacterium (Example 3, FIG. 1). Additionally, when the antimicrobial composition was applied to tempeh, a fermented food, it was confirmed that the antimicrobial composition can maintain the effect of controlling food poisoning bacteria (Example 4), while embodying the traditional flavors, and thus can be used directly in all foods including fermented foods.

As even another aspect to achieve the objects above, the present application provides a pharmaceutical composition for preventing or treating microbial infectious diseases, which includes the antimicrobial composition.

As used herein, the term "prevention" may refer to all actions that suppress or delay the onset of microbial infectious diseases by administration of the pharmaceutical composition for preventing or treating microbial infectious diseases according to the present application to a subject.

As used herein, the term "treatment" may refer to all actions that alleviate or beneficially change the symptoms of microbial infectious disease by administration of the composition to a subject suspected of having microbial infectious diseases.

As used herein, the term "improvement" may refer to all actions that at least reduce a parameter related to the condition to be treated, for example, the degree of a symptom.

As used herein, the term "subject" may refer to all of the animals, including humans, who currently have or are at risk of having microbial infectious diseases.

In particular, the microbial infectious disease is a disease caused by infection by microorganisms, and preferably, it may be a disease caused by infection by fungi or bacteria.

In one embodiment of the present application, the fungus may be *Aspergillus oryzae, Aspergillus niger*, or a combination thereof, but is not limited thereto.

In one embodiment of the present application, the bacterium may be *Bacillus cereus, Escherichia coli*, or a combination thereof, but is not limited thereto.

In one embodiment of the present application, the microbial infectious disease may be any one or more selected from the group consisting of food poisoning, diarrhea, vomiting, enteritis, gastroenteritis, constipation, abdominal pain, and abdominal distention, but is not limited thereto.

In one embodiment of the present application, an enhanced antimicrobial activity against *Bacillus cereus*, a bacterium that can cause food poisoning, and a specific antimicrobial activity against enteropathogenic *Escherichia coli* were confirmed, and additionally, a specific antifungal activity against *Aspergillus oryzae* and *Aspergillus niger*, which are fungi, was confirmed, and thus, the antimicrobial composition of the present application can be effectively used in the pharmaceutical composition for preventing or treating microbial infectious diseases.

The pharmaceutical composition for preventing or treating microbial infectious diseases according to the present application may further include a pharmaceutically acceptable carrier, and may be formulated with the carrier to be provided as food, health functional food, pharmaceuticals, quasi-drugs, feed additives, drinking water additives, etc.

As used herein, the term "pharmaceutically acceptable carrier" may refer to a carrier or diluent which does not inhibit the biological activities or properties of a compound to be administered to an organism without causing irritation to the organism.

The type of carrier that can be used in the present application is not particularly limited, and any pharmaceutically acceptable carrier commonly used in the art can be used. Non-limiting examples of the carrier may include saline, sterile water, Ringer's solution, buffered saline, an albumin injection solution, a dextrose solution, a maltodextrin solution, glycerol, ethanol, etc. These can be used alone or in a mixture of two or more thereof.

Additionally, other conventional additives such as an antioxidant, a buffer, and/or a bacteriostatic agent may be further added as necessary, and the composition may be formulated into injection formulations, such as an aqueous solution, a suspension, an emulsion, etc., pills, capsules, granules, or tablets by additionally adding a diluent, a dispersant, a surfactant, a binder, a lubricant, etc.

The administration mode of the composition for preventing or treating microbial infectious diseases according to the present application is not particularly limited, and may be carried out according to a method commonly used in the art. As non-limiting examples of the administration mode, the composition may be administered orally or parenterally. The composition for preventing, improving, or treating microbial infectious diseases of the present application may be prepared in various formulations according to a desired administration mode.

As the pharmaceutical administration forms of the antimicrobial substance of the present application, it may also be used in the form of a pharmaceutically acceptable salt thereof, and may be used alone or in combination with other pharmaceutically active compounds as well as in suitable assemblage.

As further another aspect to achieve the objects above, the present application provides a method for preventing or treating microbial infectious diseases, including administering the composition for preventing or treating microbial infectious diseases into a subject. As used herein, the term "subject" may refer to all of the animals, including humans, who currently have or are at risk of having microbial infectious diseases.

Specifically, the prevention or treatment method of the present application may include a step of administering the composition in a pharmaceutically effective amount to a subject who currently has or is at risk of having microbial infectious diseases.

The total daily dose suitable for the composition including the extract should be determined within appropriate medical judgment by a physician, and the composition may be administered once or several times in divided doses. However, for the purpose of the present application, the specific therapeutically effective dose for any particular patient may be preferably applied differently, depending on various factors including the kind and degree of the response to be achieved, specific compositions including whether other agents are occasionally used therewith or not, the patient's age, body weight, general health conditions, sex, and diet, administration time, administration route, secretion rate of the composition, duration of treatment, other drugs used in combination or concurrently with the specific composition, and similar factors well known in the medical arts.

The antimicrobial substance of the present application may be administered to mammals such as rats, mice, livestock, humans, etc. by various routes. All modes of administration may be expected; for example, the composition may be administered by an oral, rectal, intravenous, intramuscular, subcutaneous, intrauterine, or intracerebroventricular injection.

As still further another aspect to achieve the objects above, the present application provides a health functional food for preventing or improving microbial infectious diseases, which includes the antimicrobial composition.

In particular, the meanings of the microbial infectious disease, prevention, and improvement are as described above.

As used herein, the term "health functional food or nutraceutical" is the same term as a food for special health use (FOSHU), a functional food, and a health food, and refers to a food which is processed to effectively exert a body-regulating function in addition to nutrient supply, thus having high medicinal and medical effects. Accordingly, the food may be prepared in various forms such as tablets, capsules, powders, granules, liquids, pills, etc. to obtain useful effects in the prevention or improvement of microbial infectious diseases.

The heath functional food may include a sitologically acceptable carrier, which is as described above.

The health functional food of the present application can be prepared using a method commonly used in the art. Raw materials and ingredients commonly added in the art may be added for the preparation of the health functional food. Additionally, the health functional food may be prepared into any formulation that is regarded as a health functional food, without limitation. The health functional food of the present application may be prepared into various formulations, and has an advantage over general drugs in that it is free of side effects which might occur upon long-term intake of drugs because it is based on food materials. Further, the heath functional food of the present application is of high portability, and thus can be ingested as an aid for promoting the prophylactic or alleviative effect on microbial infectious diseases.

Specifically, the food may be a food prepared by adding the antimicrobial composition to food materials such as beverages, teas, flavors, gums, confectionaries, etc., or prepared as a capsule, powder, suspension, etc., and for example, it can be used for various foods, beverages, gums, teas, vitamin complexes, health functional foods, etc.

The food may be prepared into formulations such as tablets, granules, powders, capsules, liquid solutions, and pills according to a preparation method known in the art, and the content of the composition according to the present application may be adjusted depending on the formulation. Additionally, there is no particular limitation on other ingredients except those containing the antimicrobial composition according to the present application as an active ingredient, and various common flavoring agents or natural carbohydrates may be included as additional ingredients.

As still further another aspect to achieve the objects above, the present application provides a quasi-drug composition including the antimicrobial composition.

As used herein, the term "quasi-drug" may refer to a product corresponding to any one selected from a textile product, a rubber product, or an analogue thereof used for the purpose of treatment, alleviation, handling, or prevention of human or animal diseases; a product which, not being a tool, a machine, or an analogue thereof, has minimal effects or does not have any effect on humans; and a preparation used for the purpose of disinfection, pest control, or a similar use thereof for the prevention of infectious diseases, which, among the products being used for the purpose of treatment, alleviation, handling, or prevention of human or animal diseases, excludes those which are not a tool, a machine, or an analogue thereof; and which, among the products being used for the purpose of rendering a pharmacological effect on the human or animal structures and functions, excludes those which are not a tool, a machine, or an analogue thereof. Additionally, the quasi-drug may include external skin applications and personal hygiene products. Examples of the quasi-drug composition may preferably include disinfecting cleaners, shower foams, mouthwash, wet tissues, detergent soaps, hand soaps, or ointments, but is not limited thereto.

The quasi-drug may include a pharmaceutically acceptable carrier, which is as described above.

The present inventors confirmed that the newly isolated *Rhizopus oligosporus* CJCC02-20 has an antimicrobial effect against the fungi and bacteria, and thus, the antimicrobial composition using the new strain can be effectively used in quasi-drugs.

As still further another aspect to achieve the objects above, the present application provides a feed composition including the antimicrobial composition.

As used herein, the term "feed" may refer to any natural or artificial diet, meal, or ingredient of the meal for animals to eat, intake, and digest.

There is no limitation on the type of feed, and any feed commonly used in the art may be used. The feed composition may include a feed additive. The feed additive of the present application corresponds to an auxiliary feed under the Control of Livestock and Fish Feed Act, and may include probiotics. Non-limiting examples of the feed include: plant-based feeds such as grains, root plants, food-processing by-products, algae, fibers, pharmaceutical by-products, fat and oils, starches, meals or grain by-products; and animal-based feeds such as proteins, inorganic substances, fat and oils, minerals, single-cell proteins, animal planktons, or foods. These feeds may be used alone or in a mixture of two or more thereof.

In particular, the feed composition including the antimicrobial composition of the present application may further include an excipient, a diluent, and an additive.

It was confirmed that the newly isolated *Rhizopus oligosporus* CJCC02-20 of the present application has the effect of simultaneously inhibiting *Aspergillus oryzae* and *Aspergillus niger*, which are fungi, and *Bacillus cereus* and *Escherichia coli*, which are food poisoning bacteria. Thus, the present application provides a feed composition having antimicrobial and antifungal activity, and can prevent microbial infectious diseases including food poisoning of livestock.

As still further another aspect to achieve the objects above, the present application provides a method for preparing the antimicrobial composition, including culturing the newly isolated *Rhizopus oligosporus* CJCC02-20 in a medium.

As used herein, the term "cultivation" means that the *Rhizopus oligosporus* CJCC02-20 of the present application is grown under appropriately controlled environmental conditions. The cultivation process of the present application can be performed in a suitable culture medium and culture conditions known in the art. Such a cultivation process may be easily adjusted for use by those skilled in the art according to the strain to be selected. Specifically, the cultivation may be a batch culture, a continuous culture, and/or a fed-batch culture, but is not limited thereto.

As used herein, the term "medium" refers to a mixture of materials which contains nutrient materials required for the cultivation of the *Rhizopus oligosporus* CJCC02-20 as a main ingredient, and it supplies nutrient materials and growth factors, along with water that is essential for survival and growth. Specifically, the medium and other culture conditions used for culturing the *Rhizopus oligosporus* CJCC02-20 of the present application may be any medium used for conventional cultivation of microorganisms without any particular limitation. However, the *Rhizopus oligosporus* CJCC02-20 of the present application may be cultured under aerobic conditions in a conventional medium containing an appropriate carbon source, nitrogen source, phosphorus source, inorganic compound, amino acid, and/or vitamin, while adjusting the temperature, pH, etc.

In the present application, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; and amino acids, such as glutamic acid, methionine, lysine, etc. Additionally, the carbon source may include natural organic nutrients such as starch hydrolysate, molasses, blackstrap molasses, rice bran, cassava, sugar cane molasses, corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more thereof, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more thereof, but are not limited thereto.

The phosphorus source may include monopotassium phosphate, dipotassium phosphate, or corresponding sodium-containing salts, etc. Examples of the inorganic compound may include sodium chloride, calcium chloride, iron chloride, magnesium sulfate, iron sulfate, manganese sulfate, calcium carbonate, etc. Additionally, amino acids, vitamins, and/or appropriate precursors may be included.

These constituting ingredients or precursors may be added to a medium in a batch culture or continuous manner, but these phosphorus sources are not limited thereto.

Additionally, the pH of a medium may be adjusted during the cultivation of *Rhizopus oligosporus* CJCC02-20 by adding a compound such as ammonium hydroxide, potassium hydroxide, ammonia, phosphoric acid, sulfuric acid, etc. to the medium in an appropriate manner. Further, during the cultivation, an antifoaming agent such as fatty acid polyglycol ester may be added to prevent foam generation. In addition, oxygen or oxygen-containing gas may be injected into the medium in order to maintain an aerobic state of the medium; or nitrogen, hydrogen, or carbon dioxide gas may be injected without the injection of gas in order to maintain an anaerobic or microaerobic state of the medium, but the gas is not limited thereto.

The medium temperature may be in a range from 20° C. to 45° C., and specifically from 25° C. to 40° C., but is not limited thereto. The cultivation may be carried out for about 10 to 160 hours, but is not limited thereto.

The method for preparing the antimicrobial composition of the present application may further include a step of preparing the *Rhizopus oligosporus* CJCC02-20 strain of the present application, a step of preparing a medium for culturing the strain, or a combination thereof (regardless of the order, in any order), for example, prior to the culturing step.

The preparation method of the antimicrobial composition of the present application may further include a step of recovering the antimicrobial substance from the culture medium (medium in which the culture was grown) or the *Rhizopus oligosporus* CJCC02-20 strain of the present application. The recovering step may be further included after the culturing step.

In particular, any antimicrobial substances are included without limitation as long as they have an antimicrobial activity produced by the *Rhizopus oligosporus* CJCC02-20 strain, and may be, for example, crude extracts or compounds, but are not limited thereto.

In the recovering step, a desired antimicrobial substance may be collected using the method of culturing a microorganism of the present application, for example, using a suitable method known in the art according to a batch culture, continuous culture, or fed-batch culture method. For example, methods such as centrifugation, filtration, treatment with a protein-crystallizing precipitant (salting-out method), extraction, ultrasonic disruption, ultrafiltration, dialysis, various kinds of chromatography such as molecular sieve chromatography (gel filtration), adsorption chromatography, ion-exchange chromatography, affinity chromatography, etc., and HPLC may be used alone or in combination, and the desired antimicrobial substances can be recovered from the medium or microorganisms using suitable methods known in the art.

Further, the method for preparing of the antimicrobial composition of the present application may further include a purification process, which may be performed using an appropriate method known in the art. In an example, when the method for preparing the antimicrobial composition of the present application includes both a recovering step and a purification step, the recovering step and the purification step may be performed intermittently (or continuously) regardless of the order or simultaneously, or may be integrated into one step, but the method is not limited thereto.

As further still another aspect to achieve the objects above, the present application provides a method for producing a fermented product, including culturing the *Rhizopus oligosporus* CJCC02-20 strain in a medium, followed by fermentation.

As still further another aspect to achieve the objects above, the present application provides a fermented product produced by the above method.

The *Rhizopus oligosporus* CJCC02-20 strain is as described above, and the step of culturing the microorganism in a medium is also as described above.

As used herein, the term "fermented product" refers to a composition obtained by culturing the microorganism of the present application.

Further, the fermented product may include a composition in the form of a liquid or powder obtained after culturing the microorganism, followed by a suitable post-treatment. In particular, the suitable post-treatment process may include, for example, a process of culturing the microorganism, a process of removing bacterial cells, a concentration process, a filtration process, and a process of mixing carriers, and may further include a drying process. In some cases, the post-treatment process may not include a purification process.

Furthermore, the "fermented composition" does not exclude cases in which a substance obtained by a non-fermentation process and/or another substance obtained by a non-natural process is further mixed, as long as the composition obtained by culturing the microorganism of the present application is contained therein.

As still further another aspect to achieve the objects above, the present application provides a feed composition including the *Rhizopus oligosporus* CJCC02-20 or a fermented product using the strain.

The *Rhizopus oligosporus* CJCC02-20 and food are as described above.

The fermented product may refer to a medium obtained by inoculating and culturing the *Rhizopus oligosporus* CJCC02-20 strain in a medium containing the main raw materials of food, or a culture including the microorganism cultured with the medium.

Additionally, the fermented product may be a culture obtained by inoculating and culturing the *Rhizopus oligosporus* CJCC02-20 strain in food materials. The food material may be grains, but is not limited thereto.

In one embodiment of the present application, the grain may be rice, barley, wheat, corn, etc., and specifically wheat, wheat bran, or rice, but is not limited thereto.

The fermented product may be comprehensively interpreted as including all of a filtrate, a diluted solution, a concentrated solution thereof, a crude product, a purified product, a dried product, a pulverized product thereof, etc., but is not limited thereto.

As still further another aspect to achieve the objects above, the present application provides a method for preparing food, including inoculating the newly isolated *Rhizopus oligosporus* CJCC02-20 strain.

The *Rhizopus oligosporus* CJCC02-20 strain and food are as described above.

In one embodiment of the present application, the method for preparing food may be a method for preparing a fermented food, including inoculating and culturing the *Rhizopus oligosporus* CJCC02-20 in grains. The fermented food obtained by inoculating and culturing the strain may be specifically Korean paste or salted fish, and more specifically tempeh or a sauce containing tempeh, but is not limited thereto.

As still further another aspect to achieve the objects above, the present application provides a feed composition including the newly isolated *Rhizopus oligosporus* CJCC02-20 strain.

The *Rhizopus oligosporus* CJCC02-20 strain and feed are as described above.

As still further another aspect to achieve the objects above, the present application provides the antimicrobial use of the composition including any one or more selected from the group consisting of the newly isolated *Rhizopus oligosporus* CJCC02-20 strain, a spore of the strain, a culture of the strain, a fermented product of the strain, a concentrate thereof, an extract thereof, and a dried product thereof.

MODE FOR CARRYING OUT THE INVENTION

Hereinafter, the constitution and effect of the present application will be described by way of Examples. However, these Examples are provided for illustrative purposes only, and the scope of the invention is not intended to be limited by these Examples.

Example 1. Isolation and Identification of Strains Producing Antimicrobial Substances For the selection of strains having antimicrobial activity, traditional tempeh was cultured in a PDA (potato dextrose agar) medium for 5 days at 30° C., and then the strain was primarily selected using morphological features of the genus *Rhizopus*. The selected strain was isolated by culturing for 5 days at 30° C. in a PDA medium containing 1,000 ppm of 5% kanamycin.

The nucleotide sequence of the 18S rRNA, ABP (ABP1) and Chitinase (Chi2) genes of the strain selected by the above process was analyzed. Each nucleotide sequence (18S rRNA: SEQ ID NO: 1, ABP1: SEQ ID NO: 2, Chi2: SEQ ID NO: 3) of the selected strain was compared with those in the GenBank database using BLAST of the NCBI.

Specifically, primers of SEQ ID NOS: 4 and 5 were synthesized based on the nucleotide sequence of the ABP1 gene, and primers of SEQ ID NOS: 6 and 7 were synthesized based on the nucleotide sequence of the Chi2 gene, and each nucleotide sequence was confirmed through PCR. As a result, the nucleotide sequence of the present strain showed 100% homology to *Rhizopus oligosporus* 18S rRNA, 99.9% to the ABP gene, and 100% to the chitinase gene.

The strain obtained from the results above was identified as a *Rhizopus oligosporus* strain, named *Rhizopus oligosporus* CJCC02-20, and deposited at the Korean Culture Center of Microorganisms (KCCM), an International Depositary Authority, under the Budapest Treaty on Dec. 9, 2020, with Accession No. KCCM12893P.

Example 2. Isolation and Purification of Antimicrobial Substances

In order to isolate the antimicrobial substance produced by the newly isolated *Rhizopus oligosporus* CJCC02-20 strain, the strain was inoculated into 10 g to 15 g of wheat bran, followed by culturing at 30° C. for 5 days and 35° C. for 1 day. The culture was diluted with 50 times by weight of distilled water and extracted for 60 minutes at 30° C. and 150 rpm. The crude extract was filtered under reduced pressure with a 5.0 μm filter paper using diatomite. The filtrate was freeze-dried at –20° C. for 48 hours and purified into a dried product.

Example 3. Antimicrobial Activity Test Against Fungi and Food Poisoning-Causing Bacteria In order to confirm whether the newly isolated *Rhizopus oligosporus* CJCC02-20 strain has an inhibitory effect on fungi and food poisoning-causing bacteria, the following antimicrobial activity experiments were conducted.

*Aspergillus oryzae*, a fermentative fungus for Korean paste, and *Aspergillus niger*, a food contaminant, were cultured in a PDA (potato dextrose agar) medium.

*Candida albicans*, a pathogenic yeast, and *Zygosaccharomyces bailii*, a food contaminant, were cultured in a YPD medium (yeast extract peptone dextrose agar).

Additionally, *Bacillus cereus*, a food poisoning-causing bacterium, enteropathogenic *Escherichia coli*, and *Bacillus subtilis* and *Bacillus velezensis*, which are fermentative bacteria for Korean paste, were cultured in a TSA (tryptic soy agar) medium.

After dissolving the antimicrobial substance dried in Example 2 in distilled water, an 8 mm diameter paper disk was placed on a plate medium coated with the indicated strain, and 30 μL of the antimicrobial substance was constantly added and cultured at 30° C. for 24 to 48 hours to observe whether or not the growth inhibition zone was produced by the antimicrobial substance produced by the isolated strain, and the results are shown in Table 1 and FIG. 1. As shown in Table 1, those denoted by "−" represent the case where the growth is not inhibited, those denoted by "+" represent the case where the diameter of the growth inhibition zone is 3 mm to 5 mm or less, those denoted by "++" represent the case where the diameter of the growth inhibition zone is 6 mm to 10 mm, and those denoted by "+++" represent the case where the diameter of the growth inhibition zone is 10 mm or more.

Further, in addition to the *Rhizopus oligosporus* CJCC02-20 strain, four *Rhizopus oligosporus* strains, which are strains isolated from the traditional tempeh (tempeh manufactured by the traditional method in Indonesia and Vietnam), were compared for the antimicrobial activity in Comparative Examples 1 to 4.

TABLE 1

| Microorganisms | Antimicrobial Activity | | | | |
| | *Rhizopus oligosporus* CJCC02-20 | *Rhizopus oligosporus* (Comparative Example 1) | *Rhizopus oligosporus* (Comparative Example 2) | *Rhizopus oligosporus* (Comparative Example 3) | *Rhizopus oligosporus* (Comparative Example 4) |
| --- | --- | --- | --- | --- | --- |
| *Aspergillus oryzae* | +++ | − | − | − | − |
| *Aspergillus niger* | +++ | − | − | − | − |
| *Escherichia coli* | +++ | − | − | − | − |
| *Bacillus cereus* | ++ | + | + | + | + |
| *Bacillus subtilis* | + | + | + | + | + |
| *Bacillus velezensis* | + | + | + | + | + |

TABLE 1-continued

| | Antimicrobial Activity | | | | |
|---|---|---|---|---|---|
| Microorganisms | *Rhizopus oligosporus* CJCC02-20 | *Rhizopus oligosporus* (Comparative Example 1) | *Rhizopus oligosporus* (Comparative Example 2) | *Rhizopus oligosporus* (Comparative Example 3) | *Rhizopus oligosporus* (Comparative Example 4) |
| *Candida albicans* | – | – | – | – | – |
| *Zygosaccharmyces bailii* | – | – | – | – | – |

As can be seen in Table 1 and FIG. 1, the purified material obtained from the *Rhizopus oligosporus* CJCC02-20 strain showed no antimicrobial activity against yeast, but showed an excellent antifungal activity that can selectively control *Aspergillus oryzae* and *Aspergillus niger*, which are fungi that are difficult to inhibit in Korean paste or general foods.

Further, it showed a selective antimicrobial activity against enteropathogenic *Escherichia coli*, and it was confirmed that it showed an excellent antimicrobial activity against *Bacillus cereus*, a food poisoning bacterium, compared to other *Rhizopus oligosporus* strains.

Example 4: Confirmation of Effect of Controlling Food Poisoning Bacteria in Fermented Product Tempeh In order to confirm the effect of controlling food poisoning bacteria in the fermented product of *Rhizopus oligosporus* CJCC02-20 identified by Example 1, 15 g to 20 g of the *Rhizopus oligosporus* CJCC02-20 strain was inoculated into wheat rice, and then cultured at 30° C. for 6 days and at 40° C. for 1 day. The culture was made into powder using a grinder.

In order to develop fermented products with diversification of grains according to the consumption trends that change every year, 4% of the culture solution powder and commercially available *Rhizopus oligosporus* strain (Ragi Tempe Raprima, Bandung Inc., Indonesia) were inoculated into steamed soybean, steamed soybean and rice, steamed soybean and wheat flour, and steamed wheat flour and mixed, and then cultured at a temperature of 30° C. for 1-2 days by adjusting the humidity to 60% to prepare tempeh, a fermented product.

The thus-cultured tempeh and commercially available traditional tempeh were cultured at 30° C. for 1 day in a *Bacillus cereus* selective medium added with TSA (tryptic soy agar), polymyxin B, and trimethoprim. It was confirmed that *Bacillus cereus* and enteropathogenic *Escherichia coli*, which are food poisoning—causing bacteria, were not detected in the tempeh inoculated with the *Rhizopus oligosporus* CJCC02-20 strain isolated in Example 1, whereas *Bacillus cereus* was detected in the tempeh inoculated with commercially available strains and the traditional tempeh (see Table 2).

TABLE 2

| Category | Tempeh using Commercially Available Strains | | | | | Tempeh using Isolated Strains | | | |
|---|---|---|---|---|---|---|---|---|---|
| | Traditional Tempeh | Soybean | Soybean + Wheat flour | Soybean + Rice | Wheat flour | Soybean | Soybean + Wheat flour | Soybean + Rice | Wheat flour |
| Protease activity (unit/g) | 300 | 82 | 103 | 83 | 118 | 114 | 134 | 113 | 145 |
| *Bacillus cereus* (CFU/g) | 100,000 | 30,000 | 10,500 | 10,200 | 40,000 | ND | ND | ND | ND |
| *Escherichia coli* (CFU/g) | 10 | ND | ND | ND | ND | ND | ND | ND | ND |

* ND: Not Detected

From the results above, it was confirmed that the *Rhizopus oligosporus* CJCC02-20 strain, which is a tempeh fermentative strain, has an excellent effect of controlling food poisoning bacteria, while embodying the traditional flavor.

Therefore, the antimicrobial composition including the novel *Rhizopus oligosporus* CJCC02-20 strain of the present application, a spore of the strain, a culture of the strain, a concentrate thereof, and a dried product thereof has excellent antimicrobial effects against fungi and food poisoning bacteria, and thus can be effectively used in foods, quasi-drugs, pharmaceuticals, etc.

Those of ordinary skill in the art will recognize that the present application may be embodied in other specific forms without departing from its spirit or essential characteristics.

The described embodiments are to be considered in all respects only as illustrative and not restrictive. The scope of the present application is therefore indicated by the appended claims rather than by the foregoing description. All changes which come within the meaning and range of equivalency of the claims are to be embraced within the scope of the present application.

DEPOSITION NO

Depository Institution: Korean Culture Center of Microorganisms
Accession No.: KCCM12893P
Deposition Date: 20201209

---

The invention claimed is:

1. A method for inhibiting growth of at least one fungus and at least one bacterium on a surface comprising
    applying a composition comprising any one or more selected from the group consisting of a *Rhizopus oligosporus* strain, a spore of the strain, a culture of the strain, a concentrate thereof, and a dried product thereof, to the at least one bacterium and the at least one fungus,
    wherein the *Rhizopus oligosporus* strain comprises SEQ ID No: 1, SEQ ID No: 2, and SEQ ID No: 3, and
    the *Rhizopus oligosporus* strain is a strain deposited under Accession No. KCCM12893P.

2. The method of claim 1, wherein the dried product comprises a freeze-dried product.

3. The method of claim 1, wherein the at least one fungus is of the genus of *Aspergillus*.

4. The method of claim 3, wherein the at least one fungus comprises one or more selected from the group consisting of an *Aspergillus oryzae*, an *Aspergillus niger*, and a combination thereof.

5. The method of claim 1, wherein the at least one bacterium comprises one or more selected from the group consisting of bacterium of the genus of *Bacillus*, bacterium of the genus of *Escherichia*, and a combination thereof.

6. The method of claim 5, wherein the at least one bacterium comprises one or more selected from the group consisting of *Bacillus cereus*, *Escherichia coli*, and a combination thereof.

7. The method of claim 1, wherein the surface is a food surface.

8. The method of claim 7, wherein the food comprises tempeh or a sauce comprising tempeh.

9. A method for disinfecting at least one fungus and at least one bacterium comprising
    applying a composition comprising any one or more selected from the group consisting of a *Rhizopus oligosporus* strain, a spore of the strain, a culture of the strain, a concentrate thereof, and a dried product thereof, to the at least one fungus and the at least one bacterium,
    wherein the *Rhizopus oligosporus* strain comprises SEQ ID No: 1, SEQ ID No: 2, and SEQ ID No: 3,
    and the *Rhizopus oligosporus* strain is a strain deposited under Accession No. KCCM12893P.

10. The method of claim 9, wherein the dried product comprises a freeze-dried product.

11. The method of claim 9, wherein the at least one fungus is of the genus of *Aspergillus*.

12. The method of claim 11, wherein the at least one fungus comprises one or more selected from the group consisting of an *Aspergillus oryzae*, an *Aspergillus niger*, and a combination thereof.

13. The method of claim 9, wherein the at least one bacterium comprises one or more selected from the group consisting of bacterium of the genus of *Bacillus*, bacterium of the genus of *Escherichia*, and a combination thereof.

14. The method of claim 13, wherein the at least one bacterium comprises one or more selected from the group consisting of *Bacillus cereus*, *Escherichia coli*, and a combination thereof.

* * * * *

SEQUENCE LISTING

```
<160> NUMBER OF SEQ ID NOS: 7

<210> SEQ ID NO 1
<211> LENGTH: 1746
<212> TYPE: RNA
<213> ORGANISM: Unknown
<220> FEATURE:
<223> OTHER INFORMATION: Rhizopus oligosporus CJCC02-20 18s rRNA

<400> SEQUENCE: 1
caagauuaag ccaugcaugu cuaaguauaa auaacuuuau auugugaaac ugcgaauggc      60
ucauuaaauc aguuaugauc uacgugacaa auucuuuacu acuuggauaa ccgugguaau     120
ucuagagcua auacaugcaa aaaagcccug acucacgaag gggugcacuu auuagauaaa     180
accaacgcgg gguaaaaccu guuucguggu gaaucauaau aauuaagcgg aucgcuggcc     240
uugagccggc gacgguccac ucgauuuucu gcccuaucau gguugagauu guaagauaga     300
ggcuuacaau gccuauaacg gguaacgggg aauuaggguu cgauuccgga gagggagccu     360
gagaaacggc uaccacaucc aaggaaggca gcaggcgcgc aaauuacccca aucccgacac     420 ggggaggguag ugacaauaca uaacaaugca gggccuuuac ggucuugcaa uuggaaugag     480
uacaauuuaa ucccuuaacg aggaucaauu ggagggcaag ucuggugcca gcagccgcgg     540
uaauuccagc uccaauagcg uauauuaaag uuguugcagu uaaaacgucc guagucaaac     600
uuuagucuua ccggcgcggu ggccuggucu ucauugauca agcucgcgu cgcuggagac      660 uccacguccg cuggcuccua guccucgugg cuaggguuuu guggacaauu accaugagca     720
aaucagagug uuuaaagcag gcuuuaagcu ugaauguguu agcauggaau aaugaaauau     780
gacuuuaguc cuauuuucgu ugguuuaggu acuauaguaa ugauuaauag aaacgguugg     840
gggcauuugu auuugcccgc uagaggugaa auucuuggau uggccgaaga caaacuacug     900
cgaaagcauu ugacccagga cguuuucauu gaucaagguc uaaaguuaag ggaucgaaga     960
cgauuagaua ccgucguagu cuuaaccaca aacuaugccg acuagagauu gggcguguuu    1020
cuuuugacuc gcucagcauc uuagcgaaag uaaaguuuuu ggguucuggg gggaguaugg    1080
gacgcaaggc ugaaacuuaa aggaauugac ggaagggcac caccaggagu ggagccugcg    1140
gcuuaauuug acucaacacg gggaaacuca ccagguccag acauaguaag gauugacaga    1200
uugaaagcuc uuucuagauu cuauggguugg uggugcaugg ccguucuuag uucgugagug    1260
auuugucugg uuaauuccga uaacgaacga gaccuuauuc ugcuaauuac acaggcuaac    1320
ucuuucgggu ugguuuaugu uuaucauuua acuguguucu uagagagacu aucugcuuga    1380
agcagaggga aguuuuaggc aauaacaggu cugugaugcc cuuagauguu cugggccgca    1440
cgcgcgcuac acugaugaag ucagcgaguu auaaccuugg ccggaaggguc uggguaaacu    1500
```

```
uuugaaacuc aucgugcugg ggauagagca uuguaauuau ugcucuucaa cgaggaauuc    1560
cuaguaagcg cgagucauca gcucgcguug auuacguccc ugcccuuugu acacaccgcc    1620
cgucgcuacu accgauugaa ugguuauagu gagcauaugg gauccgcaga auuugacugg    1680
caacagucau uuucugcaga gaacuauggc aaacuaggcu auuuagagga aguaaaaguc    1740
guaaca                                                               1746

<210> SEQ ID NO 2
<211> LENGTH: 1268
<212> TYPE: DNA
<213> ORGANISM: Unknown
<220> FEATURE:
<223> OTHER INFORMATION: Rhizopus oligosporus CJCC02-20 ABP1 gene

<400> SEQUENCE: 2
agctgtagtg caatgttcaa gctaaaaata agtttgtgta tgtgctctgc aactgcatga      60
tattctagaa cgactgtgtt gcattttctt ttaattgatc tgtttgttgg tttctagaag     120
taatgcaaaa acggttgtac aaacatacaa aaggtcatat gacagatacg ccatcctaat     180
aagcgaaata gtgagcacct gcaagggcat tttaattaat aaagtgactt aatagcaatt     240
atggggcttt caagcttcca gggggtattt tgtttattgc ttaagaaaag tgctgtcctt     300
gtattcaaaa gtctatattt ttttgttata taaatataca catggatcac taaactattt     360
cttggaggta cagagaaaga gaggggaagg aagaacacga tccagcatca tggtcgctat     420
ggtgtcactt cgtcaacaga cgtcatttta gctcacccctt ctctcctttc tcttttttctc    480 gcttgtcttc ctttttttagt aatgttatac atttaagcgg tttatgtggt accttgccat     540
ttacataaat aaggaagctc aagattttgc aagatgctag ttctttctca aatgaagttg     600
atctacgttt tttgtttctt tactttgctc ttaattgcta ctcaacaagt gagtgctgca     660
tgtggtgctg aaggttcatg tcatggtttc ggaggcggag agttgtgtaa tgacagatgc     720
aaacgatgct ctggccctac tggaaaatac aaacggggag cctgttgtgg tactttgaaa     780
caagcttgct gctgctatta cagctaatta atgatgtgat gtgtttaact ttataaagca     840
gttgctttat aaaattgaaa attgaaaaat aaaaatgtct gtctccactc ctctgtcttc     900
ttgtttgggg tttttaattca tatgtagacg tgttacatgc tctaattatc aattacagca     960
aatgatcatc aagaggcagc agggtgtaat gaaaaacaca agtccaacac ttagagagct    1020 catttttttgc gtttttgcgc ctcaaatgaa atgcaataat ttcgttcaat caaagcttttt   1080 tttggatttt aatatgtaca agattgtaca gccattatac tattacaatc aaataaagcc    1140
tatttctctt ttcttgtttc ttctatttaa gcatttccaa cattcaaaag caagttagag    1200
ccttcgccct taccactagg taaataagcc actttggagg tttgtgataa tgtctgtgca    1260
atatcctt                                                             1268

<210> SEQ ID NO 3
<211> LENGTH: 2119
<212> TYPE: DNA
<213> ORGANISM: Unknown
<220> FEATURE:
<223> OTHER INFORMATION: Rhizopus oligosporus CJCC02-20 chi2 gene

<400> SEQUENCE: 3
gcatgcgcat agtaaacaat gcttaaacca gatgacatac atacgtctat gaatgcaact     60
gattgatcat gaaatagccg cttctttgtt ttcgaatgat atccctacca tttcttcctt    120
```

```
tttatttcaa tgtaacatga gttttaatag gtaatatatt acttgatatt attacttgat     180
attacctatg accctaatct tattcattaa cgtgtaactt gagctgcaat gggaaaaaaa     240
aagataatga agacatggca acattagccc acgcatataa atactcactg gacatcctga     300
catcaaatca ttatctttac acttttcttt cccttattct tcaacatgct cactcgtact     360
ttccttggaa tggctatatc tgccttcttg gcatcaactg gtgttcaagc tgcttggtcc     420
tctcatggcc ctaatgtcat gtactactgg ggtcaaaatt ctgctggcgg atcaaataca     480
caagcatcct taggcactta ctgtgagtct ggccaagtcg atgccgtcct cctgtccttc     540
cttcacgtct ttaacgttgg tggtatccct gaaatcaatc tttctagcgc ctgtgctggt     600
acctattttc ccaatactca actacttagt tgtcctgctg ttggtgctgg taagtgttaa     660
accttttgtt gtcggggtct cttaacatct ctttcttgat agatatcaag aaatgtcaag     720
acaagggcgt caaggtcata ctctctcttg gtggtgctgc tggtgtctat ggtttcacaa     780
gcgatgccca aggacaacag ttcgcacaga cgatctggaa cctctttggt ggtggaaact     840
cagacacacg tccatttggt gatgctgtta ttgacggtgt cgatcttgac attgaaggtg     900
gctcatctac gggttatgtc gcctttgtga atgctcttcg tcaaaagttc tccagcaact     960
tccttattgg tgctgctcct caatgcccct tccctgacgc catcctcggc agtgtgttga    1020
actcggctag tttcgactac gtcaatgttc agttctataa caactattgc tctgctactg    1080
gttcctcctt caactttgac acctgggata actgggccaa gacgacgtca cctaacaaga    1140
acgtcaagat catgtttacg gttcctggct catctactgc tgcaggcagc ggctacgttc    1200
ccatgtctac tcttcaaact atagttcctt ctcttgcttc caagtactcc agctacggcg    1260
gtgtctcagt ctgggatgcc tctcaagcct ggaataacgg tggcttcaac tctcaactct    1320
actcgcttgt ccacagcggt ggctccactc ctcctcctcc ttcctcttct tcagctacca    1380
agacaacaac aaaaacgaca gcaacaagca ccaagacgac gactacgact gcccctactg    1440
ctaccagcac acctggcagt tgtcctgttg ccaatcagcc ttgctctact caaaatcaat    1500
atgcttgtac agccgatggc aagtacgctg tctgcgacca tggcaaatgg gttgcctcct    1560
cctgcccctc caacactgtc tgcattccta ctaccgatgg tgcctctatc tactgtggtt    1620
atgctactgg ctctggcagc acttgtcctt cagtcagcgc actcgaaatt acagctgctt    1680
ctctcggctc taagaatggc cccgtacctc gcccatacaa ggcttccaag gttgctgctc    1740
aactcgctgt tacttccact gacaagaata gctttgaagc tgttatcaat gctcgtcgca    1800
ccacgctcac tcccttttgaa aaatctgtta ctatcgaatt cactacacct tccaacatca    1860
agtttaccga atctgatatg ggtcccgttc gtcaagtcgg caacaaggtt cgtattcaag    1920
ccaagaatga ttataacgaa tccatgactc tcgtcgtcaa agtcaagggt tccatcaatt    1980
caggcgtctt tgtggctccc agtacttctg cttggaactt aaataaaata ttgtattaga    2040
taataataat aataaaaaaa gtgcaataac gtttttattgt acgtattgaa gcagatttat    2100
gtgtattata ttattaaaa                                                  2119
```

<210> SEQ ID NO 4
<211> LENGTH: 21
<212> TYPE: DNA
<213> ORGANISM: Artificial Sequence
<220> FEATURE:
<223> OTHER INFORMATION: ABP1 gene reading pair forward primer

<400> SEQUENCE: 4

```
gagaaagaac tagcatcttg c                                                 21
```

-continued

```
<210> SEQ ID NO 5
<211> LENGTH: 16
<212> TYPE: DNA
<213> ORGANISM: Artificial Sequence
<220> FEATURE:
<223> OTHER INFORMATION: ABP1 gene reading pair reverse primer

<400> SEQUENCE: 5
catcattaat tagctg                                                    16

<210> SEQ ID NO 6
<211> LENGTH: 23
<212> TYPE: DNA
<213> ORGANISM: Artificial Sequence
<220> FEATURE:
<223> OTHER INFORMATION: chi2 gene reading pair forward primer

<400> SEQUENCE: 6
caacatgctc actcgtactt tcc                                            23

<210> SEQ ID NO 7
<211> LENGTH: 21
<212> TYPE: DNA
<213> ORGANISM: Artificial Sequence
<220> FEATURE:
<223> OTHER INFORMATION: chi2 gene reading pair reverse primer

<400> SEQUENCE: 7
gagccacaaa gacgcctgaa t                                              21
```